United States Patent [19]

Capiau et al.

[11] Patent Number: 6,106,842
[45] Date of Patent: Aug. 22, 2000

[54] EXTRACTION OF CELL-BOUND PROTEIN FROM BORDETELLA

[75] Inventors: Carine Capiau, Harveng Mons; Martin Comberbach, Genval; Piet Roelants, Rosières, all of Belgium; Jean Petre, Sienna, Italy

[73] Assignee: SmithKline Beecham Biologicals, Rixensart, Belgium

[21] Appl. No.: 08/513,768

[22] PCT Filed: Feb. 28, 1994

[86] PCT No.: PCT/EP94/00597

§ 371 Date: Oct. 23, 1995

§ 102(e) Date: Oct. 23, 1995

[87] PCT Pub. No.: WO94/20538

PCT Pub. Date: Sep. 15, 1994

[30] Foreign Application Priority Data

Mar. 4, 1993 [GB] United Kingdom ............. 9304399

[51] Int. Cl.[7] .................... A61K 39/00; A61K 39/02; A61K 39/10; C12P 1/00
[52] U.S. Cl. ........................... 424/240.1; 424/184.1; 424/234.1; 435/71.2; 435/41; 530/825; 530/820
[58] Field of Search ............... 424/240.1, 184.1, 424/234.1; 435/71.2, 41; 530/825, 820

[56] References Cited

U.S. PATENT DOCUMENTS

| | | | |
|---|---|---|---|
| 3,405,218 | 10/1968 | Haskell et al. ............... | 424/92 |
| 3,465,078 | 9/1969 | Spiesel ............... | 424/92 |
| 3,862,109 | 1/1975 | Mitsuda et al. ............... | 260/112 R |
| 4,464,474 | 8/1984 | Coursaget et al. ............... | 436/513 |
| 4,988,798 | 1/1991 | Blum et al. ............... | 530/399 |
| 5,101,014 | 3/1992 | Burns et al. ............... | 530/350 |
| 5,276,142 | 1/1994 | Gotto ............... | 530/413 |

FOREIGN PATENT DOCUMENTS

| | | |
|---|---|---|
| 0162639 | 11/1985 | European Pat. Off. ....... A61K 39/10 |
| 0 437 687 | 7/1991 | European Pat. Off. . |
| WO 91/15505 | 10/1991 | WIPO . |

OTHER PUBLICATIONS

Collingwood, T.N., et al., *Journal of Biochemical and Biophysical Methods*, 17:303–310 (1988).
Milburn, P., et al., *Enzyme Microb. Technol.*, 12:527–532 (Jul. 1990).
Vorauer–Uhl, K., et al., *Bioseparation*, 3:217–226 (1993).
Brennan, et al., Identification of a 69–Kilodalton Nonfimbrial Protein As an Agglutiogen of *Bordetella pertussis*, (1988), *Infection and Immunity*, vol. 56, pp. 3189–3195.
Petersen, et al., "Proliferative Responses To Purified and Fractionated *Bordetella pertussis* Antigens in Mice Immunized With Whole–Cell Pertussis Vaccine", (1993), *Vaccine*, vol. 11, pp. 463–472.
Magnarelli et al. Journal of Infections Diseases 159(1):43–49, 1989.
Armstrong et al. Journal of Bacteriology 166(1): 212–16, 1986.
Capiau et al. Proceedings of the Sixth International Symposium on Pertussis 1990, pp. 75–86.
Rosenbusch et al. Journal of Biol Chem 249:8019–29, 1974.
Gabay et al. Journal of Bacteriology 162(1):85–91, 1985.
Armstrong et al. Journal of Bacteriology 166(1): 212–16, 1986.
Capiau et al. Proceedings of the Sixth International Symposium on Pertussis 1990, pp. 75–86.
Mortimer EA, "Pertussis Vaccine", In Plotkin SA.
Mortimer EA eds. *Vaccines*, Philadelphia, WB Saunders Co., 1988.
Novotny et al. Journal of Infectious Diseases 164:114–22, 1991.
Rosenbusch et al. Journal of Biol Chem 249:8019–29, 1974.
Gabay et al, Journal of Bacteriology 162(1):85–91, 1985.
Englard et al. Precipitation Techniques. In: Guide to Protein Purification. Methods in Enzymology, vol. 182.
MP Deutscher (ed). Academic Press, Inc. New York. 1990.

*Primary Examiner*—James C. Housel
*Assistant Examiner*—V. Ryan
*Attorney, Agent, or Firm*—Shanks & Herbert

[57] ABSTRACT

The present invention discloses a process for extracting a cell-bound protein of bacterial origin, useful in acellular vaccines, comprising contacting a suspension of the cell-bound protein with a flocculating agent prior to heat treatment.

19 Claims, 3 Drawing Sheets

SDS - PAGE

W. BLOT

SDS - PAGE

W. BLOT

LANES: 1 2 3 4 5 6 7 8

SDS - PAGE

LANES: 1 2 3 4 5 6 7 8

← 69kDa

W. BLOT

EXTRACTION OF CELL-BOUND PROTEIN FROM BORDETELLA

This application is a 371 of PCT/EP94/00597 filed Feb. 28, 1994 which claims priority to foreign application 9304398.0 filed in Great Britain on Mar. 4, 1993.

The present invention relates to a novel process for the isolation of cell proteins having utility as antigenic factors of component or acellular vaccines. In particular, the invention relates to a novel process for the extraction of outer membrane proteins of bacterial organisms, for example the outer membrane protein of *Bordetella pertussis*, which has a molecular weight of approximately 69,000 Daltons and is generally referred to as the 69 kD protein of *Bordetella pertussis*, or pertactin.

Whooping cough, or pertussis, is a highly-infectious disease which primarily affects children. In addition to causing respiratory complications, whooping cough may result in nerve damage and a high incidence of mortality, particularly in children from low socioeconomic groups and in newborn infants who do not possess maternal anti-pertussis antibodies. The etiologic agent of pertussis is the Gram-negative coccobacillus, *Bordetella pertussis*. The bacteria are believed to invade the respiratory tract and induce a toxic state which remains even after their disappearance, several days later.

The disease is currently controlled through immunisation with "whole cell" vaccine prepared by growing the *Bordetella pertussis* organism in fermenters and then inactivating the resulting cells by heat treatment and/or addition of chemical agents. Although the World Health Organisation presently recommends the immunisation of infants to prevent the incidence and spread of pertussis, concern has arisen over the reported adverse events resulting from various vaccine formulations. The consequent reduced usage of conventional *B. pertussis* vaccine has resulted in an increase in the incidence of pertussis infections. The need for a pertussis vaccine which avoids the reported adverse events from whole cell vaccine is recognised. Considerable research effort has accordingly been put into the development of an efficaceous acellular vaccine comprising a small number of highly-purified antigenic proteinaceous components.

A number of antigens have been proposed as acellular vaccine components, including for example lymphocytosis promoting factor (LPF), also known as histamine sensitising factor, islet activating protein or, more commonly, pertussis toxin (PT); filamentous hemagglutinin (FHA); and fimbrial agglutinogens.

A further potential antigen is one of the outer membrane proteins of the bacterium, having a molecular weight of approximately 69,000 Daltons (pertactin) found in all virulent strains of *B. pertussis*. The *B. pertussis* 69 kD protein is immunologically-related to similar proteins having slight differences in electrophoretic mobility which are produced by the human pathogen *B. parapertussis* and the animal pathogen *B. bronchiseptica*. Although the 69 kD protein is secreted in relatively small amounts into the fermentation broth during the cultivation of *B. pertussis*, the majority of it is found attached to the cell membrane, from which it may be readily extracted. Published procedures for the extraction and purification of the 69 kD protein do not however allow for large-scale commercial production of a highly-purified and stable antigen.

EP-0 162 639 describes acid-glycine extraction of the cells followed by several purification steps culminating in an affinity chromatography separation using a specific monoclonal antibody. The protein obtained has been reported to have both poor stability and adenylate cyclase activity, and the downstream purification procedure is not suitable for large-scale production.

Brennan et al. (Infection and Immunity 56, 3189–3195, 1988) describe a further method whereby protein is released from cells by heat treatment and a protein extract is obtained which is purified by chromatography on fetuin-Sepharose and a monoclonal antibody affinity column.

U.S. Ser. No. 7/308,864 describes extraction and purification involving heat treatment and centrifugation, followed by DEAE-Sepharose ion-exchange chromatography and protein-specific, dye-ligand gel chromatography. This method avoids the use of expensive monoclonal antibodies but is nevertheless regarded as inappropriate for large-scale production. One particular problem which has been identified is the small quantity of 69 kD protein released into solution as a percentage of the total protein released after the heat treatment. EP-A-0 437 687 sets out to improve the efficiency of release of 69 kD protein from the culture broth by using a repetitive extraction process involving a plurality of extraction steps in series.

The present invention overcomes the problem of inefficient protein recovery by providing a process which enhances the yield of protein released from the microbial cells after a single extraction step and also obviates the requirement for subsequent centrifugation to remove the cell debris. Furthermore, the process of the present invention has the additional advantage that it effectively eliminates most of the high molecular weight endotoxins (lipopolysaccharides) which are present in the culture broth after fermentation and are further released into solution when the membrane proteins are extracted by application of heat. Heat treatment of microbial cell suspensions following fermentation is an important step in the isolation of proteins, for example outer membrane proteins, which are poorly secreted by the microbes into the culture broth during fermentation. The 69 kD protein of *B. pertussis* is typical of such outer membrane proteins which are secreted in insufficient quantity to warrant direct isolation from the broth supernatant at production scale. In this respect it differs from the other antigen candidates for an acellular pertussis vaccine, pertussis toxin (PT) and filamentous haemagglutinin (FHA).

Heat treatment involves heating the cell suspension in buffer at, for example, 60° C. for approximately one hour, during which time the outer membrane proteins slough off the cell membrane into solution. The solution is not however a free-flowing liquid but is largely a glutinous, jelly-like mass comprising dead cells and the contents therefrom, which can be separated (by for example, filtration or centrifugation) from the free-flowing liquid on a small scale (5–10 ml aliquots) only with difficulty. This heavily-hydrated jelly frequently contains more than 50% of the original liquid volume and would, if discarded, considerably reduce the yield of 69 kD protein. Coarse filtration is moreover unsatisfactory because the jelly immediately blocks the filter and effectively prevents passage of liquid.

The present invention provides an effective method for eliminating the formation of a jelly-like mass during the heat treatment. It has been found that addition of a flocculating agent to the cell suspension prior to heat treatment causes an intense flocculation of the cells to take place. The flocculated mass of cells can be readily separated from the suspending broth, and may be washed to remove unwanted broth components before heat treatment. The dead cells re-flocculate after heat treatment, leaving a substantially cell-free supernatant containing the majority of soluble protein. This procedure gives a high-percentage recovery of the desired protein, in solution, for downstream purification.

The present invention confers yet further advantage in that it can provide recovered protein which has to be subjected to less-stringent downstream purification because most of the high molecular weight endotoxins are eliminated from the protein-containing solution obtained after heat treatment together with the flocculated mass of dead cells. The possibility therefore exists for reducing the number of downstream purification steps required to achieve the requisite standard of protein purity demanded for prophylactic and therapeutic applications.

The present invention accordingly provides for a process for extracting cell-bound protein of bacterial origin comprising contacting a suspension of the cell-bound protein with a flocculating agent.

A wide range of flocculating agents well known in the art may be employed in the process of the invention to improve the handling qualities of the cell suspension following heat treatment. Preferred flocculating agents for use in the present invention are materials embodying divalent cations. Suitable divalent cations for use in the invention are made available from salts of barium, calcium and strontium, for example halide salts such as barium chloride, calcium chloride or strontium chloride, preferably barium chloride.

The flocculating agent is suitably brought into contact with a suspension of cells under controlled-pH conditions and the liquid volume is adjusted by addition of appropriate buffer. After mixing the flocculated cells are allowed to settle. The flocculated cells are suitably collected by sedimentation (or centrifugation) and may be washed with saline or buffer before exposure to heat treatment.

The extraction process of the invention, when used in conjunction with further downstream processing, gives rise to 69 kD protein from *B. pertussis* with a very high level of purity. It has, for example, no detectable levels of PT or heat-labile toxin, and endotoxin levels are reduced to nanograms per mg of protein. In addition, the protein has none of the enzyme activity, in particular adenylate cyclase activity, associated with earlier production methods.

In a preferred embodiment of the invention, 69 kD protein is produced in a fermentation broth or culture of *B. pertussis*. Suitable strains for use in the invention are described and are readily available in commercial collections such as the American Type Culture Collection, Rockville, Md., USA. Preferred strains are those which are capable of growing in liquid culture media, and of producing high yields of 69 kD protein.

Examples of strains which may be employed include, without limitation, *B. pertussis* phase I, *B. pertussis* phase II, *B. pertussis* phase I CS, *B. pertussis* Tohama, *B. pertussis* strain 185-30, *B. pertussis* strain 18323, *B. pertussis* strain 134, *B. pertussis* strain 509, *B. pertussis* strain Wellcome 28, and Office of Biologics *B. pertussis* strain 165. A preferred strain for use in the present invention is *B. pertussis* phase I, Tohama, which is available from the Institute of Fermentation, Osaka, Japan under accession number IFO-14073.

For use in the present invention the selected *B. pertussis* strain can be grown in a variety of ways known to persons skilled in the art. Various cultivation methods are known which employ different cultivation steps, and liquid or solid media, depending on the quantity and origin or conservation methods of the seed culture. However, any known method will suffice for use in the present invention which provides an inoculum of a conventionally-acceptable size for large-scale production.

A suitable medium for growth of a *B. pertussis* inoculum may be selected by any person skilled in the art. Suitable media include, without limitation, Gengou medium (EP-A-0 077 646); the media described in N. Andorn et al. (Appl. Microbiol. Biotechnol., 28, 356–360, 1988) and references cited therein; Stainer-Scholte medium (J. Gen. Microbiol., 63, 211–220, 1971); modified Stainer-Scholte medium described in A. Imaizumi et al (Infect. Immun., 41, 3, 1138–1143, 1983 and J. Microbiol. Methods, 2, 339–347, 1984); Verway medium (U.S. Pat. No. 4,784,589); synthetic medium B2 (P. Van Hemert; Prog. Indust. Microbiol.; (Bull, M. J. ed.), Vol 13, p. 151, Elsevier Sci., Amsterdam (1977)) or described modifications thereof.

For growth of *B. pertussis* culture which is a starting material of the present invention, an inoculum is added to a suitable liquid medium and fermentation is conducted employing conventional fermentation methods and fermenter designs known in the art. Persons skilled in the art will appreciate that different results may be obtained depending upon the selection of a particular combination of conventional fermenter design, fermentation medium, method and parameters. Preferred combinations for use in the present invention are those suitable for use in large-scale production. Examples of such combinations of methods, designs and media are exemplified in EP-A-0 077 646 and preferably EP-A-0 121 249 and EP-A-0 239 504.

After completion of the fermentation, the *B. pertussis* fermentation broth is suitably processed to remove the antigenic factors PT and FHA which are secreted directly into the broth, for example by the method described in EP-A-0 427 462 by adsorption on hydroxyapatite, the methodology of which is incorporated herein by reference.

The residual microbial suspension containing the cell-bound 69 kD protein is then treated with a flocculating agent according to the present invention before being subjected to heat treatment in order to effect release of the protein.

It has been found that residual endotoxin levels may be minimised by controlling the pH of the supernatant. By routine experimentation, the optimum pH for any chosen flocculating agent may be selected. Thus, the pH of the supernatant is suitably adjusted to between 4 and 10, preferably between pH 8.5 and 9.5, by addition of base, either before or after addition of an aqueous solution of for example a halide salt of barium, calcium or strontium, preferably barium chloride. The liquid volume may be adjusted by addition of buffer, suitably TRIS buffer. Suitably mixing is carried out for approximately 5 minutes and the resulting slurry is allowed to flocculate over a period of approximately 1 hour. The supernatant containing the unused components of the growth medium (salts, aminoacids, minerals, etc.) and other proteinaceous materials and endotoxins released into the broth during fermentation may then be separated and discarded, and the flocculate may be washed with further buffer or saline. Alternatively, the flocculated cells may be separated by centrifugation before washing.

Since the high concentration of salts, amino acids and minerals present in the fermentation broth may interfere with subsequent purification steps, the flocculation/washing process may be repeated as many times as is necessary to obtain a slurry of flocculated cells in which the concentration of halide salt has been reduced to an acceptable level, for example, approximately 0.02% w/v.

The slurry of flocculated cells is then subjected to heat treatment at a temperature of approximately 60° C. for 15–60 minutes during which time the 69 kD protein is liberated into the liquid suspension and the bacteria are killed. After cooling, for example at approximately 4° C. for an appropriate duration, preferably overnight, the dead cell mass is removed, for example by decantation or centrifugation, and the supernatant is filtered and stored under sterile conditions at reduced temperature, for example at about 4° C.

The 69 kD protein may then be subjected to downstream purification using appropriate techniques known in the art. Preferably, the 69 kD protein is purified using a combination of ion-exchange, hydrophobic interaction and size-exclusion chromatography. Suitable chromatographic supports include anion-exchange such as DEAE-Sepharose, Q-Sepharose, SP-Sepharose, CM-Sepharose; hydrophobic interaction such as Butyl-, Phenyl-, Octyl-Sepharose, TSK; and gel filtration such as Sephacryl, Sepharose, Sephadex, Superose, Superdex, etc.

The highly-purified 69 kD protein may be sterilised by filtration and, if necessary subjected to diafiltration.

The antigenic identity of purified 69 kD outer membrane protein isolated according to the above-described process may be determined by techniques well known in the art, for example using SDS-PAGE (Sodium Dodecyl Sulphate-Poly Acrylamide Gel Electrophoresis) and Western blot analysis using a monoclonal antibody. Purity may be qualitatively assessed by SDS-PAGE. Quantitative analysis may be carried out using ELISA (Enzyme Linked Immuno Sorbent Assay) or HPLC.

Purified 69 kD protein produced according to the invention has been shown by ELISA testing to have PT and FHA content below the sensitivity limit of the test. No PT activity (CHO cells) was detectable. Endotoxin levels are less than 0.1 units/mcg protein by the LAL-CS (Limulus Amoebocyte Lysate-Chromogenic Substrate) test. The 69 kD protein has no detectable adenylate cyclase activity and the Western blot analysis for adenylate cyclase is negative.

The resulting 69 kD protein has utility as an antigenic component of an acellular vaccine which may be administered to elicit a protective antibody response against infection by *B. pertussis*. Such a vaccine may be prepared by conventional techniques. For example, a vaccine may be prepared comprising antigenic factors and a suitable conventional carrier in an aqueous solution buffered to physiological pH for direct use. Alternatively, antigenic factors may be adsorbed onto a conventional adjuvant, such as aluminium hydroxide or aluminium phosphate. In addition, one or more *B. pertussis* antigens, including the 69 kD protein, may be combined with further immunogens to prepare multi-functional vaccines, capable of inducing protection against more than one pathogen.

The present invention has particular utility as part of an overall process for the isolation and purification of several protein antigen candidates for an acellular pertussis vaccine from a single fermentation of *B. pertussis*. Thus PT, FHA and 69 kD protein can each be isolated in pure form from the same fermentation broth for incorporation in a single pertussis vaccine. The *B. pertussis* fermentation broth is suitably processed according to the method described in EP-A-0 427 466 to isolate PT and FHA, and the residual supernatant is processed as herein described to provide 69 kD protein. Pertussis toxin may be toxoided according to the method described in WO 91/12020 which is incorporated herein by reference. The antigen components which have been purified separately may be adjuvanted separately and subsequently pooled.

The extraction of cell-bound protein and the removal of endotoxins from solution by addition a flocculating agent, preferably a divalent cation, is not limited to the isolation of outer membrane protein, such as pertactin, from pathogenic Bordetella organisms, such as *Bordetella pertussis*. The process of the invention has utility in any biological process involving the production of prophylactic or therapeutic outer membrane proteins. Typical examples of other biological processes which may benefit from the invention are:

a) the production of outer membrane proteins from meningitidis species such as *Neisseria meningitidis*;

b) the production of pili and agglutinogens from *Escherichia coli*;

c) the production of outer membrane proteins from haemophilus species such as *Haemophilus influenzae*, d) the production of outer membrane proteins from borrelia species such as *Borrelia burgdorferi*, and e) the production of outer membrane proteins from streptococcus species such as strains of Group A and Group B streptococcus.

Biological products obtainable according to the process of the invention are not restricted to proteins for human use. Typical examples of further processes which may derive benefit are the isolation of outer membrane proteins for use in:

f) the production of vaccines against rhinitis, which affects pigs and is caused by *Bordetella bronchiseptica* and *Haemophilus pleuropneumoniae*;

g) the production of a vaccine against colibacillosis, which affects pigs and is caused by *Escherichia coli*; and h) the production of an antigen for an ELISA test against leptospirosis which affects domestic animals, calves and humans.

The process of the invention is illustrated, but not limited, by the following Examples which relate to the extraction of the 69 kD outer membrane protein from *Bordetella pertussis*.

EXAMPLE 1

Flocculation Trials

A strain of *B. pertussis* Tohama was cultured under controlled fermenter conditions to provide a suspension of cells of sufficient quantity to extract PT and FHA from the supernatant by adsorption on hydroxyapatite gel. The remaining cell suspension was subjected to the following steps:

1) The suspension was cooled to 4° C., and divided into 50 mL sample aliquots.

2) One of each of the following flocculants was added to each sample to give a final concentration as indicated: dextran T500 (10 g/L), calcium chloride (10 g/L), methanol (20%), and polyethylene glycol 50000 (10 g/L).

3) Each sample was vigorously mixed whilst the pH was adjusted to a pre-determined value (dextran T500, pH 5; calcium chloride, pH 4 and 9; methanol, pH 6; polyethylene glycol 50000, pH 5). The samples were then left to flocculate without mixing at 4° C.

4) The supernatants were decanted off and replaced with equal volumes of TRIS buffer at a concentration of 125 mM. After resuspension, the samples were heated to, and maintained at 60° C. in a water bath for a duration of 1 hour. Each sample was shaken regularly (every 5 minutes) to ensure an even temperature distribution.

5) After cooling to 4° C. in the absence of agitation, the dead cells re-flocculated. After centrifugation, the supernatant from each sample was tested, not only for the presence of 69 kD protein by SDS-PAGE, Western blot and ELISA, but also for the presence of contaminating endotoxins using the LAL-CS test.

Figure 1:
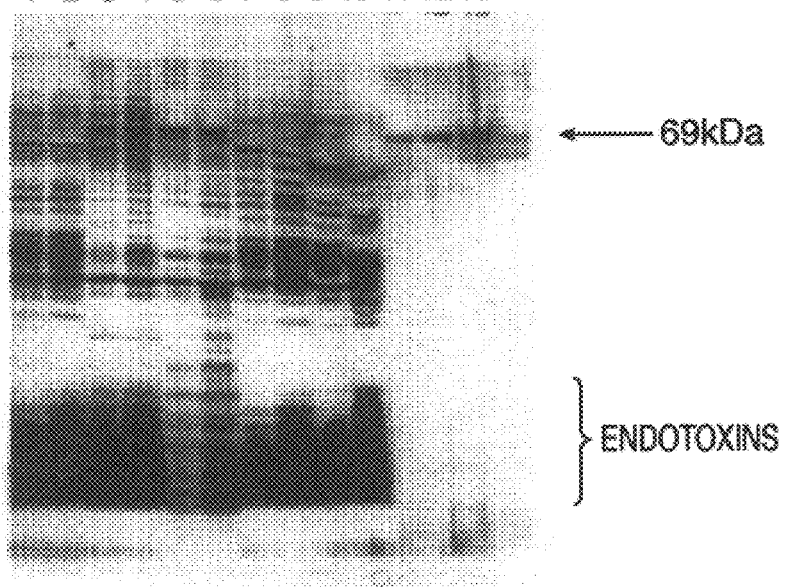
FIG. 1 shows the results (SDS-PAGE) for the flocculation trials of four flocculating agents tested in Example 1 against purified 69 kD protein.
Figure 2:
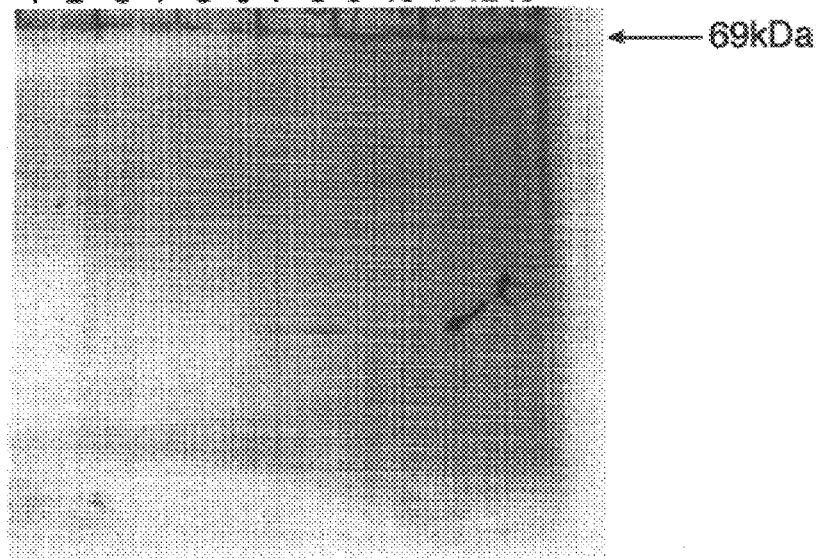
FIG. 2 shows the results (Western blot) for the flocculation trials of four flocculating agents tested in Example 1 against purified 69 kD protein.

The results of the SDS-PAGE and the Western blot are given in FIGS. 1 and 2, respectively. Each sample (corresponding to one flocculant) was loaded onto the gel and the blot using two adjacent lanes, corresponding to the volumes 15 and 45 µL. The remaining three lanes were loaded with successively-increasing volumes (6.8, 13.6, and 27.2 µL) from a pool of purified 69 kD protein at a concentration of 55 mg/L. The legend for the lanes in the gel and the Western blot can be seen in the following table:

TABLE 1

| Lane No | Sample No | Flocculant | Concentration | pH | Volume loaded (µL) |
|---|---|---|---|---|---|
| 1 | 1 | Dextran | 10 g/L | 5 | 15 |
| 2 | | | | | 45 |
| 3 | 2 | CaCl$_2$ | 10 g/L | 4 | 15 |
| 4 | | | | | 45 |
| 5 | 3 | CaCl$_2$ | 10 g/L | 9 | 15 |
| 6 | | | | | 45 |
| 7 | 4 | MeOH | 20% | 6 | 15 |
| 8 | | | | | 45 |
| 9 | 5 | PEG | 10 g/L | 5 | 15 |
| 10 | | | | | 45 |
| 11 | 69kD pool | | | | 6.8 |
| 12 | | | | | 13.6 |
| 13 | | | | | 27.2 |

The results of the ELISA and the LAL-CS tests can be seen in the following table:

TABLE 2

| Sample No | Flocculant | Concentration | pH | ELISA (mg/L) | Endotoxin (mg/L) |
|---|---|---|---|---|---|
| 1 | Dextran | 10 g/L | 5 | 24.3 | >15 |
| 2 | CaCl$_2$ | 10 g/L | 4 | 22.8 | >15 |
| 3 | CaCl$_2$ | 10 g/L | 9 | 20.3 | <15 |
| 4 | MeOH | 20% | 6 | 27.5 | >15 |
| 5 | PEG | 10 g/L | 5 | 31.1 | >15 |

FIGS. 1 and 2 show the presence and location of the 69 kD protein in the majority of samples. The presence of 69 kD protein is confirmed by the result from the ELISA test shown in table 2 above.

Although flocculation occurred with CaCl$_2$ at both pH 4 and 9, lanes 5 and 6 on the gel (FIG. 1) show a particularly striking example of the reduced level of endotoxins present in the supernatant after treatment with CaCl$_2$ at pH 9. This was confirmed by the results from the LAL-CS test shown in table 2 above.

EXAMPLE 2

Choice of Divalent Cation

Flocculation trials using the methodology described in Example 1 were carried out using the following halide salts at a concentration of 10 g/L and a pH of 9: calcium chloride, barium chloride and strontium chloride.

Figure 3:
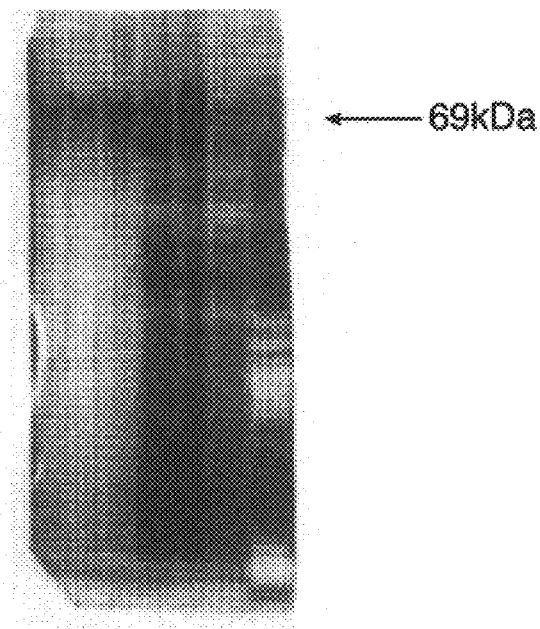
FIG. 3 shows the results (SDS-PAGE) for the flocculation trials of three flocculating agents tested in Example 2 against purified 69 kD protein and a non-flocculated control.
Figure 4:
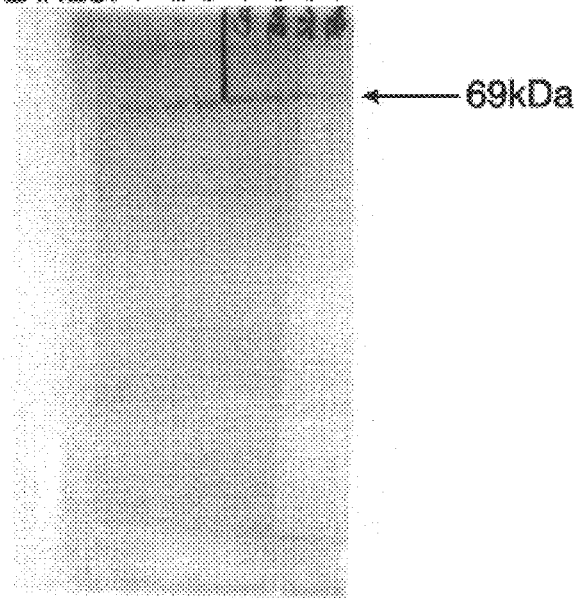
FIG. 4 shows the results (Western blot) for the flocculation trials of three flocculating agents tested in Example 2 against purified 69 kD protein and a non-flocculated control.

The results of the SDS-PAGE and the Western blot are given in FIGS. 3 and 4 respectively. The first three lanes were loaded with successively-increasing volumes (6.8, 13.6, and 27.2 µL) from a pool of purified 69 kD protein at a concentration of 55 mg/L. The last lane was loaded with a non-flocculated control sample of the cell suspension. The legend for the lanes in the gel and the Western blot can be seen in the following table:

TABLE 3

| Lane No | Sample No | Flocculant | Volume loaded (µL) |
|---|---|---|---|
| 1 | 69kD pool | | 6.8 |
| 2 | | | 13.6 |
| 3 | | | 27.2 |
| 4 | 1 | CaCl$_2$ | 45 |
| 5 | 2 | BaCl$_2$ | 45 |
| 6 | 3 | SrCl$_2$ | 45 |
| 7 | 4 | Control | 45 |

The results of the ELISA test can be seen in the following table:

TABLE 4

| Sample No | Flocculant | ELISA (mg/L) |
|---|---|---|
| 1 | CaCl$_2$ | 15.1 |
| 2 | BaCl$_2$ | 15.8 |
| 3 | SrCl$_2$ | 8.6 |
| 4 | Control | 13.5 |

FIGS. 3 and 4 show the presence and location of the 69 kD protein in all of the samples. The 69 kD protein band observed in the control sample (lane 7) was substantially less dense than those bands from samples which were flocculated with divalent cations (lanes 4, 5 and 6), indicating a substantially-lower concentration of 69 kD protein in the supernatant from a non-flocculated sample.

The low 69 kD protein concentration given in the ELISA test in Table 4 gave the impression that strontium was a less effective cation than either calcium or barium, but this observation was not reflected in either the gel (FIG. 3) or the blot (FIG. 4).

However, the 69 kD concentrations observed in the supernatants of samples flocculated with either calcium or barium were substantially equal in the ELISA test, and gave 69 kD protein bands of similar density in both the gel and the blot.

The flocculation process, as observed visually, with reference to the rate of flocculation and the morphology of the flocs, was slightly more effective with barium than with calcium or strontium.

EXAMPLE 3

Flocculation and Washing Procedure

Flocculation and washing was carried out using the following procedure:

1) The cell suspension remaining after the extraction of PT and FHA was cooled to 4° C., and divided into four sample aliquots of 50 mL. One sample was set aside as the control.

2) Barium chloride was added to the three remaining samples to give a final concentration of 10 g/L, and each suspension was mixed vigorously whilst the pH was adjusted to 9 using a suitable base.

3) The suspensions were then left to flocculate without mixing at 4° C.

4) The supernatants were decanted off each pellet, and three different concentrations of TRIS buffer (125, 50, or 20 mM) were added to each pellet (one concentration per pellet) to give a final volume of 50 mL.

5) After resuspension, the three samples were then left to flocculate a second time without mixing at 4° C.

6) The procedure given in 4) and 5) above was repeated as many times as necessary to dilute the concentration of barium chloride down to approximately 0.2 g/L.

7) The control sample was centrifuged at 10,000×g for 1 hour, and the supernatant was decanted off and replaced with an equal volume of TRIS buffer at a concentration of 125 mM.

8) After a final resuspension in TRIS buffer of the required concentration, all the samples (including the control) were heated to, and maintained at 60° C. in a water bath for a duration of 1 hour. Each sample was shaken regularly (every 5 minutes) to ensure an even temperature distribution.

9) After cooling all the samples to 4° C. in the absence of agitation, the dead cells in the samples containing barium chloride re-flocculated, and those in the control sample were re-centrifuged at 10,000×g for 1 hour.

10) The supernatant from each sample (including the control) was tested for the presence of 69 kD protein by SDS-PAGE, Western blot and ELISA.

Figure 5:
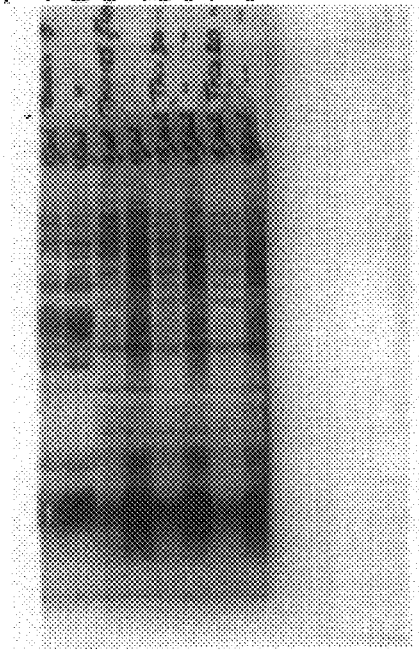
FIG. 5 shows the results (SDS-PAGE) for the flocculation trials with barium chloride described in Example 3.
Figure 6:
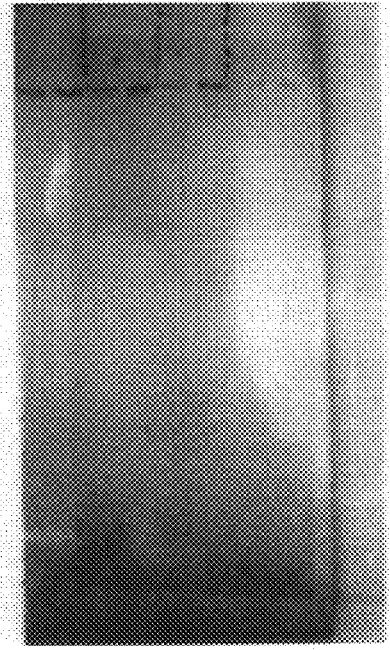
FIG. 6 shows the results (Western blot) for the flocculation trials with barium chloride described in Example 3.

The results of the SDS-PAGE and the Western blot are given in FIGS. 5 and 6, respectively. Each sample was loaded onto the gel and the blot using two adjacent lanes, corresponding to the volumes 15 and 45 µL. The legend for the lanes in the gel and the Western blot can be seen in the following table:

TABLE 5

| Lane No | Samples | Volume loaded (µL) |
| --- | --- | --- |
| 1 | Control | 15 |
| 2 | | 45 |
| 3 | TRIS 125 mM | 15 |
| 4 | | 45 |
| 5 | TRIS 50 mM | 15 |
| 6 | | 45 |
| 7 | TRIS 20 mM | 15 |
| 8 | | 45 |

The results of the ELISA test can be seen in the following table:

TABLE 6

| Samples | ELISA (mg/L) |
| --- | --- |
| Control | 30 |
| TRIS 125 mM | 22 |
| TRIS 50 mM | 24 |
| TRIS 20 mM | 33 |

FIGS. 5 and 6 show the presence and location of the 69 kD protein in all of the samples. The presence of 69 kD protein was confirmed by the results from the ELISA test shown in table 6 above.

The presence and similarity in the concentrations of 69 kD protein found in the supernatants of suspensions subjected to repeated flocculation and washing steps described above, indicated that a major reduction in the ionic strength of the suspending broth, resulting from the application of this technique, did not adversely influence the extraction and the yield of 69 kD protein from *B. pertussis*.

In addition, the effectiveness of barium chloride as a flocculent at concentrations as low as approximately 0.2 g/L in the supernatant was demonstrated.

What is claimed is:

1. A process for isolating a cell-bound outer membrane protein of bacterial origin in a microbial cell comprising:
    (a) contacting a microbial cell suspension comprising a cell bound protein with a flocculating agent to form a flocculent mass prior to heating;
    (b) removing said flocculent mass from said suspension; and
    (c) heating said flocculent mass to release the protein from the microbial cell.

2. The process of claim 1, wherein said process further comprises the step of isolating the protein.

3. The process of claim 1, wherein said contacting step and said removing step are repeated.

4. A process for isolating a cell-bound outer membrane protein of bacterial origin in a microbial cell comprising:
    (a) contacting a microbial cell suspension comprising a cell bound protein with a flocculating agent to form a flocculent mass prior to heating; and
    (b) heating said flocculent mass to release the protein from the microbial cell.

5. The process of claim 4, wherein said process further comprises the step of isolating the protein.

6. The process of claim 4 or 5, wherein the cell-bound protein is an outer membrane protein of a Bordetella, Haemophilus, Escherichia, Streptococcus or Borrelia species.

7. The process of claim 6, wherein the outer membrane protein is the 69 kD protein of *Bordetella pertussis*.

8. The process of claim 4, wherein the flocculating agent is a material embodying a divalent cation.

9. The process of claim 8, wherein the flocculating agent is a barium, calcium or strontium salt.

10. The process of claim 9, wherein the salt is barium chloride.

11. The process of claim 4, wherein the cell-bound protein is suspended in a supernatant at a pH in the range 4 to 10.

12. A process as claimed in claim 1 wherein the cell-bound protein is an outer membrane protein of a Bordetella, Haemophilus, Escherichia, Streptococcus or Borrelia species.

13. A process as claimed in claim 1 wherein the outer membrane protein is the a 69 kD protein of *Bordetella pertussis*.

14. A process as claimed in claim 1 wherein the flocculating agent is a material embodying a divalent cation.

15. A process as claimed in claim 14 wherein the flocculating agent is a barium, calcium or strontium salt.

16. A process as claimed in claim 15 wherein the salt is a halide.

17. A process as claimed in claim 16 wherein the salt is a chloride.

18. A process as claimed in claim 17 wherein the salt is barium chloride.

19. A process as claimed in claim 1 wherein the cell-bound protein is suspended in a supernatant at a pH in the range 4 to 10.

* * * * *